United States Patent

Gerlach et al.

[11] 4,033,904
[45] July 5, 1977

[54] INTERCHANGEABLE SPECIMEN TRAYS AND APPARATUS FOR A VACUUM TYPE TESTING SYSTEM

[75] Inventors: Robert L. Gerlach, Los Altos; George D. Rossini, Mountain View, both of Calif.

[73] Assignee: Varian Associates, Inc., Palo Alto, Calif.

[22] Filed: Dec. 24, 1975

[21] Appl. No.: 644,284

Related U.S. Application Data

[63] Continuation of Ser. No. 453,749, March 22, 1974, abandoned.

[52] U.S. Cl. .................. 250/491; 250/141; 250/442
[51] Int. Cl.² .................................. G21K 5/06
[58] Field of Search .......... 250/440, 441, 442, 309, 250/310, 492, 491

[56] References Cited

UNITED STATES PATENTS

| | | |
|---|---|---|
| 2,849,619 | 8/1958 | Eisfeldt .................. 250/442 |
| 3,342,992 | 9/1967 | Schmidt et al. ........... 250/441 |
| 3,374,349 | 3/1968 | Macres .................. 250/310 |
| 3,400,265 | 9/1968 | Houbart .................. 250/441 |
| 3,496,359 | 2/1970 | Weinstock et al. ......... 250/310 |
| 3,629,579 | 12/1971 | Naiton .................. 250/310 |
| 3,679,900 | 7/1972 | Kimura .................. 250/441 |
| 3,689,766 | 9/1972 | Freeman ................. 250/492 |

*Primary Examiner*—Alfred E. Smith
*Assistant Examiner*—B. C. Anderson
*Attorney, Agent, or Firm*—Stanley Z. Cole; Leon F. Herbert; Edward H. Berkowitz

[57] ABSTRACT

The vacuum chamber for an Auger analyzer is provided with a side access port through which interchangeable specimen trays are inserted and installed on a rotatable support structure. The specimen tray has a plurality of peripheral specimen sites and a Faraday cup probe structure similarly positioned but affixed to the support structure. The Faraday cup facilitates calibrating the ion beam and positioning the ion beam and the cup at the focal point of the electron beam. The support structure is subsequently rotated to sequentially expose each specimen to the beams.

16 Claims, 7 Drawing Figures

1

INTERCHANGEABLE SPECIMEN TRAYS AND APPARATUS FOR A VACUUM TYPE TESTING SYSTEM

This is a continuation of application Ser. No. 453,749 filed March 22, 1974, abandoned.

FIELD OF THE INVENTION

This invention relates to vacuum systems for examining specimens on trays and more particularly to such systems with interchangeable specimen trays.

DESCRIPTION OF THE PRIOR ART

Heretofore specimen trays for Auger analyzers had a plurality of specimen sites without a provision for a test probe. In order to calibrate the apparatus the specimen tray was removed and a test probe installed and carefully positioned at the focal point of the electron beam. This prior art procedure is inconvenient and involved separate vacuum runs for calibration and for operation. Further, these prior art specimen trays were formed as an integral part of the bulky interior supporting structure which is suspended from the top plate of the vacuum chamber. In order to remove the specimen tray, the top plate had to be unbolted and lifted off along with the internal support structure, i.e., the specimen tray support, the test probe and associated cables, and the precision translation apparatus used for adjusting the position of the specimens.

The removed apparatus was bulky and delicate, requiring considerable time to remove and properly support outside the chamber. The specimens were then mounted on the tray which remained secured to the supporting structure. The removed apparatus was then repositioned into the chamber and pump down was initiated. Establishing the required operating vacuum was prolonged because of the substantial ingassing of the chamber interior surface and the removed support surface during the down time in which these surfaces were exposed to the atmosphere. In addition, during the dismounting, transporting and remounting, the precision apparatus was exposed to atmospheric contaminants and to physical damage.

It is therefore an object of this invention to provide an improved vacuum type examining apparatus.

It is another object of this invention to provide a vacuum type apparatus for examining specimens mounted on specimen trays which are interchangeable and are conveniently and quickly removed and replaced.

It is an additional object of this invention to provide a vacuum type apparatus for examining specimens in which the down time and the pumping time are minimized.

It is still another object of this invention to provide a vacuum type apparatus for examining specimens which is easily tested or calibrated and which may be tested or calibrated in the same vacuum run as the operational examination.

It is yet a further object of this invention to provide a vacuum type system for examining specimens in which the specimen tray has a void space corresponding to a specimen site for accomodating a test probe.

It is even another object of this invention to provide an Auger analyzing system in which the angle of the specimen relative to the electron gun may be changed.

BRIEF DESCRIPTION OF DRAWINGS

Further objects and advantages of the vacuum examining apparatus and the interchangeable specimen trays will become apparent from the following detailed description taken in conjunction with the following drawings in which.

DESCRIPTION OF THE PREFERRED EMBODIMENTS

Figure 1:
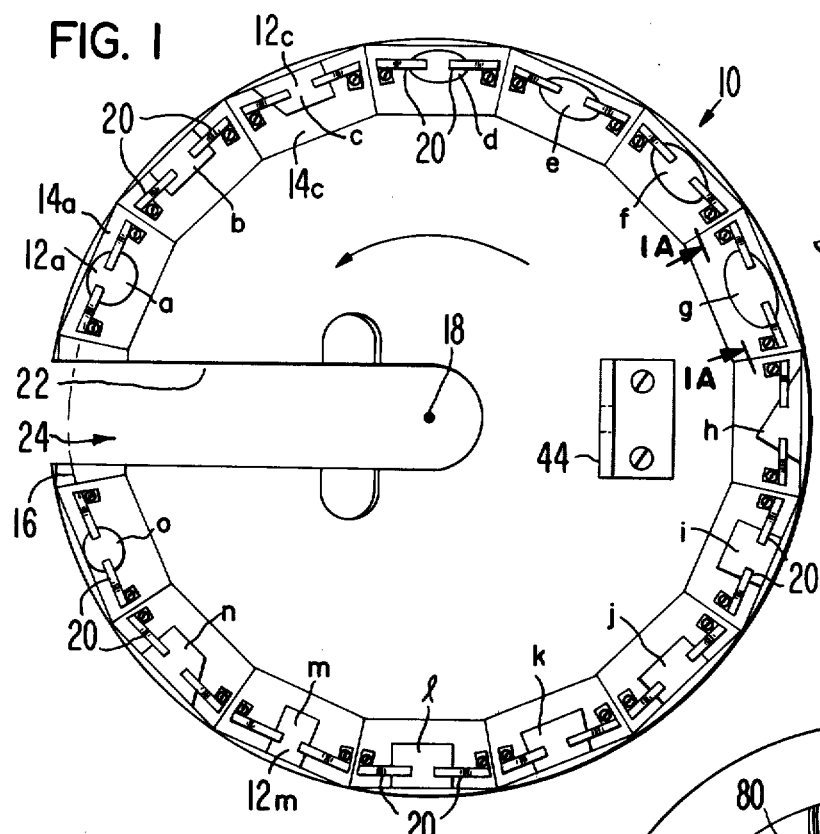
FIG. 1 is a top view of an interchangeable specimen tray showing a plurality of specimens mounted in a circle with a void provided for accommodating a test probe.
Figure 1A:
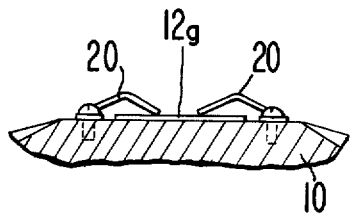
FIG. 1A shows a sectional view of one of the specimen holders.
Figure 2:
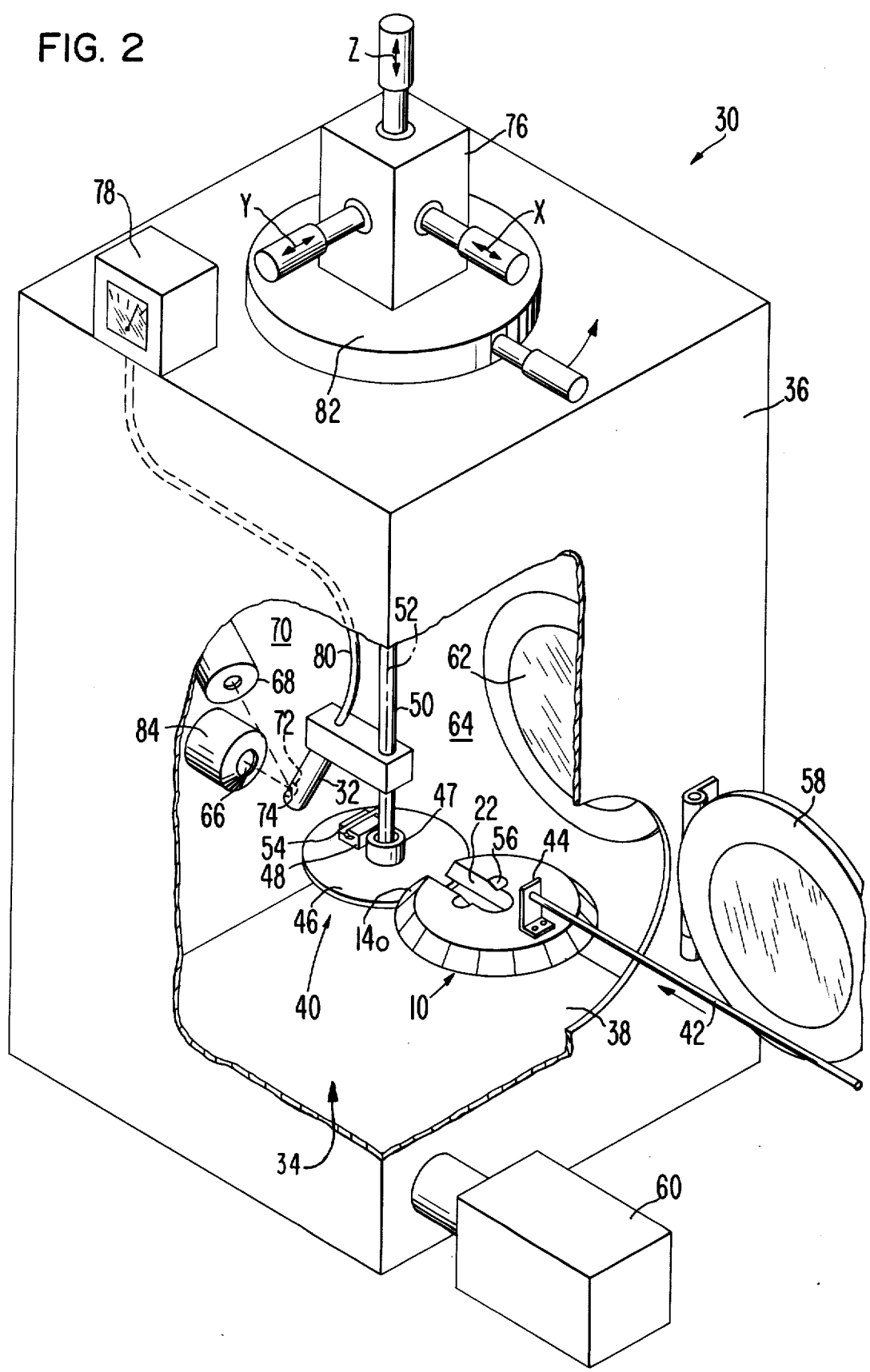
FIG. 2 is an isometric view of an Auger analyzing apparatus broken away to show the specimen tray of FIG. 1 being installed on the carousel supporting structure.

FIG. 1 shows one example of a specimen tray 10 with a plurality of specimens 12a–o mounted on a plurality of target zones 14a–o. Target zones 14 are located along a circle 16 (indicated in dotted lines) having a center 18 generally central to specimen tray 10. In the example of FIG. 1A specimens 12 are retained by clips 20 shown more clearly in the expanded fragmentary portion of FIG. 1. Also in the example in FIG. 1 target zones 14 are bevelled flats about the periphery of specimen tray 10. A slot 22 is provided for indexing specimen tray 10 as it is installed into the Auger analyzing apparatus 30 as shown in FIG. 2. Slot 22 encompasses circle center 18 and creates a void 24 along the circle 16 for accommodating a testing probe 32 shown in FIGS. 3 and 4.

Figure 3:
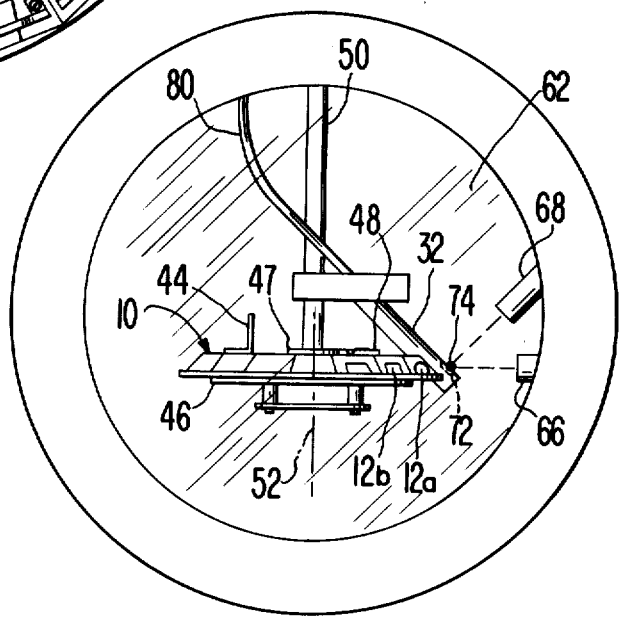
FIG. 3 is a view of the installed specimen tray in the calibration position as seen through the window provided in the back wall of the apparatus of FIG. 2.

FIG. 2 shows the specimen tray 10 being installed in a vacuum chamber 34 formed by vacuum envelope 36 of apparatus 30. Tray 10 is inserted into vacuum chamber 34 through an access port 38 onto a rotatable support structure or carousel 40. Tray 10 is suitably handled without contamination of the tray or the interior or apparatus 30 by a metal rod 42 which engages a handling bracket 44 extending from tray 10. Tray 10 is positioned on a base 46 of carousel 40 by slot 22 which engages a guide collar 47 and indexing guide 48, which extend upwardly from base 46. Base 46 and guide 48 are suspended from shaft 50. Carousel 40 is rotatable on shaft 50 about an axis 52 which is coincident with circle center 18 of tray 10 when the tray is fully positioned as shown in FIG. 3. Test probe 32 is mounted on carousel 40 immediately behind guide 48 to occupy void 24 of fully positioned tray 10. Tray 10 is secured by a suitable device such as spring fingers 54 extending from the top of guide 48 and engaging a notch 56 in the top surface of tray 10. Access port 38 is then closed by a suitable cover plate such as hinged door 58 and vacuum chamber 34 is pumped down by pump 60 to the desired operating pressure. Installed tray 10 may be seen through a window 62 in back wall 64 of vacuum envelope 36. FIG. 3 shows tray 10 in the test or calibrate position as viewed from window 62. An electron gun 66 and an ion gun 68 are mounted on a side wall 70 of vacuum chamber 34 proximate test probe 32. During calibration of Auger analyzing apparatus 30, a suitable detector such as a Faraday cup 72 mounted on the end of test probe 32 is positioned at the focal point 74 of electron gun 66 by an X-Y-Z translating apparatus 76. Probe 32 is moved to focal point of electron gun and analyzer by techniques well known to those in the field. Ion gun 68 is then mechanically positioned or electrostatically focused to intersect the electron beam of gun 66 at its focal point 74. The proper positioning of the ion beam is determined by maximizing the response on measuring instrument 78.

Figure 4:
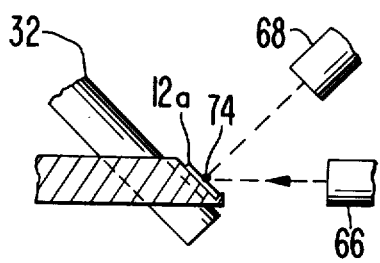
FIG. 4 is a view of the specimen tray of FIG. 3 in the examining or operating position with a specimen exposed to the beams.

Carousel 40 is then turned by rotating apparatus 82 to rotate tray 10 about circle center 18, displacing test probe 32 from total point 74 and positioning target zone 14a at focal point 74. FIG. 4 shows tray 10 in the operating or examining position. It may be necessary to translate specimen 12a along the axis to accommodate for the thickness of the specimen in order to place the surface of specimen 12a at focal point 74. Ion gun 68 is then operated to clean or etch the surface of specimen 12a and in turn electron gun 66 is operated to produce Auger electrons characteristic of specimen 12a which are identified by an analyzing device 84. If desired, guns 66 and 68 may be scanned to cover an area of specimen 12a and ion gun 68 may be used to sputter a depth profile of specimen 12a. Carousel 40 is then turned to sequentially position specimens 12b–o at focal point 74 for Auger analysis. Each specimen 12 is mounted on a target zone 14 which lies along circle 16 and is equidistant from circle center 18. Circle center 18 is now coincident with rotating axis 52 and as carousel 40 is rotated the specimens move along circle 16, and each specimen 12 is positioned at focal point 74 just as test probe 32 was so positioned during calibration. Each specimen 12 must be translated along the X axis to compensate for the individual thickness of the specimen and for any eccentricity of shaft 50.

Figure 5A:
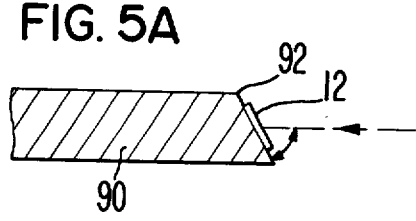
FIG. 5a is a side view of a modified specimen tray having a steep angle relative to the electron beam for examining conductive material.

FIG. 5a shows a modified specimen tray 90 having target zones 92 tilted at a steep angle with respect to the electron beam which is the preferred relationship for analyzing conductive material.

Figure 5B:
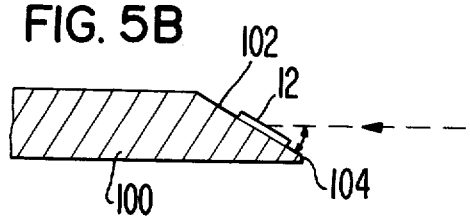
FIG. 5b is another modified specimen tray having a shallow angle with respect to the electron beam for examining insulative materials.

FIG. 5b shows another modified specimen tray 100 having target zones 102 tilted at a shallow angle with respect to the electron beam, which is preferred for analyzing insulative materials. Specimen trays 90 and 100 are completely interchangeable with specimen tray 10 of FIG. 1. FIG. 5b also shows an insulative layer 104 on the bottom of specimen tray 100 for establishing electrical isolation between specimen tray 100 and carousel 40.

The objects of this invention have been accomplished by providing a set of interchangeable specimen trays which may be quickly and easily mounted and removed from the examining apparatus. As the first set of specimens is being processed in the apparatus on the first specimen tray, the second set of specimens is being prepared and mounted on the second specimen tray. The apparatus is brought to atmospheric pressure and the specimen trays are quickly exchanged through the door. The apparatus is again pumped down to operating pressure. Because the specimen trays exchange time is minimum, less ingassing occurs during the exposure to the atmosphere and consequently less outgassing is required during pump down. Further, the delicate translation apparatus remains within the heavy protective vacuum envelope and is not subject to fouling or misalignment. More significantly, the permanent provision of a calibrating probe positioned along the specimen circle permits the apparatus to be calibrated at the beginning of each run or at any time during each run.

It will be apparent to those skilled in the art that various changes may be made in the apparatus and specimen trays described without departing from the scope of the invention. For example, this invention may be used with radiation other than electrons. The detector on the test probe may be responsive to other types of radiation such as light, x-ray, etc., which are emitted by a local radiation source for various testing and examination besides Auger analysis. Accordingly, the scope of this invention should be determined only by the wording of the following claims and their legal equivalents.

What is claimed is:

1. In apparatus for examining samples: vacuum envelope means defining a vacuum chamber, an axially elongated shaft rotatively mounted in the chamber, a radially extending sample holder support affixed to the shaft, a sample holder removably mounted on the support coaxially of the shaft and having a radially extending slot in which the shaft is received, said sample holder having a plurality of sample receiving zones spaced peripherally of the holder a predetermined distance from the center thereof, a sealable aperture in the envelope means permitting installation and removal of the sample holder, a test probe constrained for rotation with the sample holder support, said test probe being positioned in the slot and aligned with the sample zones, a radiation source for directing radiation to a stationary target zone at the periphery of the sample holder, means for rotating the shaft and support to rotate the sample holder and thereby selectively align the test probe or one of the sample zones with the target zone, and examining means responsive to the effect of radiation on a sample in the target zone.

2. The apparatus of claim 1 wherein the sample holder comprises a disk-like member with the sample receiving zones disposed on axially inclined tangentially extending faces at the periphery of the member.

3. The apparatus of claim 1 further including means for releasably securing the sample holder in a predetermined position on the support.

4. The apparatus of claim 1 wherein the shaft extends vertically and is suspended from the upper portion of the chamber.

5. The apparatus of claim 1 further including means for adjusting the position of the shaft, support and holder in an axial direction and in two directions orthogonal to the axis of the shaft.

6. In apparatus for examining samples: means defining a vacuum chamber, a rotatable support mounted in the chamber for receiving a sample holder and rotating the same about an axis, a disk-shaped sample holder removably mounted on the support and having a plurality of axially inclined tangentially extending sample receiving surfaces spaced a predetermined distance from the axis of rotation, a test probe affixed to the support and spaced from the axis by the predetermined distance, said test probe being aligned in a radial plane with the sample receiving surfaces, means for directing radiation to a stationary target zone spaced the predetermined distance from the axis, the sample receiving surfaces and the test probe being selectively aligned with the target zone by rotation of the support, and examining means responsive to the effect of radiation on a sample in the target zone.

7. In apparatus examining examiniang samples: means defining a vacuum chamber, a support mounted in the chamber for receiving a sample holder, a sample holder removably mounted on the support and having a plurality of sample receiving surfaces, a test probe affixed to the support, means for directing radiation to a focal position within the chamber, means for moving the support relative to the focal position to selectively locate the probe or any one of the sample receiving surfaces in a position facing the focal position, and means for moving the support relative to the focal position to selectively position the probe or the surface of any sample on the sample holder at a location coinciding with the focal position.

8. The apparatus of claim 7 wherein the sample holder includes a radially extending slot in which the test probe is positioned.

9. The apparatus of claim 7 wherein the support comprises a vertically extending shaft suspended from the upper portion of the chamber and a radially extending base affixed to the shaft on which the sample holder is mounted, the sample holder having a radially extending slot in which the shaft is received.

10. The apparatus of claim 9 further including an indexing guide on said base for reception in said slot.

11. The apparatus of claim 7 further including means for releasably securing the sample holder in a predetermined position on the support.

12. In an apparatus for examining the radiation scattering properties of an incident radiation upon a selectable one of a plurality of samples: wall means defining a vacuum chamber, a shaft rotatably mounted on said wall means and projecting into said chamber, a support mounted on said shaft, a disk-shaped specimen tray having a plurality of sample receiving surfaces arranged in a circle, said tray being removably mountable on said support, a test probe mounted for rotation with said shaft at a fixed radial distance from the axis of said shaft, said test probe being sensitive to said incident radiation and said specimen tray having a slot in its periphery which passes around the axis of said shaft when said specimen tray is mounted on said support.

13. In apparatus for examining samples as claimed in claim 12 further comprising a door closing an opening in said wall means, said opening being positioned adjacent said support whereby said specimen tray can be moved through said opening for positioning on and removal from said support.

14. In apparatus for examining samples as claimed in claim 13 further comprising an indexing guide on said support and radially aligned with said probe, said guide being receivable within said slot to guide said slot for alignment with said probe.

15. In apparatus for examining samples as claimed in claim 14 further comprising latch means cooperating between said indexing guide and said specimen tray to releaseably hold said tray in operating position on said support.

16. In apparatus for examining samples as claimed in claim 12 further comprising means for moving said shaft along its axis and for translating said shaft in two directions orthogonal to said axis.

* * * * *